(12) United States Patent
Harti et al.

(10) Patent No.: US 11,819,530 B1
(45) Date of Patent: Nov. 21, 2023

(54) LONG TERM TREATMENT OF HAIR LOSS

(71) Applicant: LEGACY HEALTHCARE (SWITZERLAND) SA, Epalinges (CH)

(72) Inventors: Saad Harti, Epalinges (CH); JiaWei Liu, Geneva (CH)

(73) Assignee: Legacy Healthcare (Switzerland) SA, Epalinges (CH)

( * ) Notice: Subject to any disclaimer, the term of this patent is extended or adjusted under 35 U.S.C. 154(b) by 0 days.

(21) Appl. No.: 18/341,980

(22) Filed: Jun. 27, 2023

Related U.S. Application Data

(60) Provisional application No. 63/467,077, filed on May 17, 2023.

(51) Int. Cl.
| | | |
|---|---|---|
| *A61K 36/8962* | (2006.01) | |
| *A61K 36/752* | (2006.01) | |
| *A61P 17/14* | (2006.01) | |
| *A61K 36/185* | (2006.01) | |
| *A61K 36/77* | (2006.01) | |

(52) U.S. Cl.
CPC ........ *A61K 36/8962* (2013.01); *A61K 36/185* (2013.01); *A61K 36/752* (2013.01); *A61K 36/77* (2013.01); *A61P 17/14* (2018.01)

(58) Field of Classification Search
None
See application file for complete search history.

(56) References Cited

U.S. PATENT DOCUMENTS 8,361,522 B2    1/2013   Ulmann et al.

FOREIGN PATENT DOCUMENTS

| | | |
|---|---|---|
| WO | WO-2008113912 A2 | 9/2008 |
| WO | WO-2012017361 A2 | 2/2012 |
| WO | WO-2012113820 A1 | 8/2012 |
| WO | WO-2012140013 A2 | 10/2012 |
| WO | WO-2013020719 A2 | 2/2013 |
| WO | WO-2015055739 A1 | 4/2015 |
| WO | WO-2015067759 A1 | 5/2015 |
| WO | WO-2017186954 A1 | 11/2017 |
| WO | WO-2019134760 A1 | 7/2019 |
| WO | WO-2021224455 A1 | 11/2021 |

OTHER PUBLICATIONS

Amersfoort. J., et al., "Immunomodulation by endothelial cells—partnering up with the immune system?" Nat Rev Immunol. 2022; 22(9): 576-588.
Askin, O., et al., "Evaluation of the alopecia areata patients on tofacitinib treatment during the COVID-19 pandemic," Dermatol Ther. 2021; 34(2): e14746.
Bertolini M, et al. "Hair follicle immune privilege and its collapse in alopecia areata. Experimental Dermatology," 2020; 29:1-23. DOI: 10.1111/exd.14155.
Conic, R.Z., et al., "Young Dermatologists Italian Network; Bergfeld WF. Comorbidities in pediatric alopecia areata," J Eur Acad Dermatol Venereol. 2020; 34(12): 2898-2901.
Coureau, B., et al., "Cushing's syndrome induced by misuse of moderate- to high-potency topical corticosteroids," Ann Pharmacother. 2008; 42(12):1903-1907.
Dillon, K.L., "A Comprehensive Literature Review of JAK Inhibitors in Treatment of Alopecia Areata," Clin Cosmet Investig Dermatol. Jun. 25, 2021; 14:691-714.
Hoisnard, L., et al., "Adverse events associated with JAK inhibitors in 126,815 reports from the WHO pharmacovigilance database," Sci Rep. May 3, 2022; 12(1):7140.
Kragstrup, T.W., et al., "Waiting for JAK inhibitor safety data," RMD Open. Feb. 2022; 8(1):e002236.
Lintzeri, D.A., et al., "Alopecia areata—Current understanding and management," J Dtsch Dermatol Ges. Jan. 2022; 20(1):59-90.
Meah N, et al. "The Alopecia Areata Consensus of Experts (ACE) study: Results of an international expert opinion on treatments for alopecia areata," J Am Acad Dermatol. Jul. 2020; 83(1):123-130. doi: 10.1016/j.jaad.2020.03.004. Epub Mar. 9, 2020.
Murphrey, B.M., et al., "NCBI Bookshelf. A service of the National Library of Medicine," National Institutes of Health. StatPearls [Internet]. Treasure Island (FL): StatPearls Publishing; Jan. 2023.
Olsen, E.A., et al., "National Alopecia Areata Foundation. Alopecia areata investigational assessment guidelines—Part II," National Alopecia Areata Foundation. J Am Acad Dermatol. Sep. 2004; 51(3):440-7.
Østbye, T., et al., "Is there time for management of patients with chronic diseases in primary care?," Ann Fam Med. May-Jun. 2005; 3(3):209-14.
Ryan, G.E., et al., "Resident Memory T Cells in Autoimmune Skin Diseases," Front Immunol. May 3, 2021; 12:652191. doi: 10.3389/fimmu.2021.652191. PMID: 34012438; PMCID: PMC8128248.
Shawky, A.M., et al., "A Comprehensive Overview of Globally Approved JAK Inhibitors," Pharmaceutics. May 6, 2022; 14(5):1001.
McGettigan, M.L., "Alopecia areata and its effects on patients," J Investig Dermatol Symp Proc. Dec. 2013; 16(1):S41.
Schimmel, L., et al., "Leukocyte transendothelial migration: A local affair. Small GTPases," Jan. 2, 2017; 8(1):1-15. doi: 10.1080/21541248.2016.1197872. Epub Aug. 15, 2016. PMID: 27715453; PMCID: PMC5331897.
Stadler, J.F., et al. "Topical corticosteroid phobia in atopic dermatitis: international feasibility study of the TOPICOP score," Allergy. 2017; 72(11):1713-1719.
Villasante Fricke AC, et al. "Epidemiology and burden of alopecia areata: a systematic review," Clinical, Cosmetic and Investigational Dermatology, 2015: 8: 397-403.
Wienke, J., et al., "T cell interaction with activated endothelial cells primes for tissue-residency," Front. Immunol. 13:827786, (2022).

(Continued)

*Primary Examiner* — Michael V Meller
(74) *Attorney, Agent, or Firm* — Harness Dickey & Pierce P.L.C.

(57) ABSTRACT

The invention relates to a method for the treatment and/or prevention of hair loss in a subject, wherein the therapeutic effects persist for at least 24 weeks or more after the last administration of the composition. Also disclosed are kits for treating and/or preventing hair loss.

18 Claims, 2 Drawing Sheets

(56) References Cited

OTHER PUBLICATIONS

Wollenberg, A., et al. "Consensus-based European guidelines for treatment of atopic eczema (atopic dermatitis) in adults and children: part II," J Eur Acad Dermatol Venereol. 2018; 32(6):850-878.
Patsner, B. & Harti, S., "A Botanical Compound for the Treatment of Alopecia Areata and Chemotherapy-Induced Alopecia," Journal of Investigative Dermatology Symposium Proceedings, 20: S69-S70 (2020).

LONG TERM TREATMENT OF HAIR LOSS

CROSS-REFERENCE TO RELATED PATENT APPLICATIONS

This patent application claims the benefit of U.S. Provisional Patent Application No. 63/467,077 filed on 17 May 2023, the entire contents of which are incorporated by reference.

FIELD

The invention relates to a method for the treatment and/or prevention of hair loss in a subject, wherein the therapeutic effects persist for at least 24 weeks or more after the last administration of the composition. Also disclosed are kits for treating and/or preventing hair loss.

BACKGROUND

The hair follicle (HF) is a unique mini organ which undergoes a continuous, lifelong regenerative cyclic process. The lower part of the healthy anagen HF (bulge and bulb) enjoys relative immune privilege (IP), which protects the hair follicle from inflammatory processes and promotes immune tolerance. These distinct HF compartments are characterized by factors that act as IP guardians to preserve the HF IP (Lintzeri, 2022).

As the hair follicle develops, blood vessels originating from the deep dermal vascular plexus surround it. These vessels nourish the hair follicle and support nutrient delivery, waste elimination, and growth (Murphey 2022). The vascular system governs guidance to traveling immune cells and thereby supports protective immune functions that keep our body free of pathogens etc. In case of inflammation or immune surveillance the cells lining the luminal site of blood vessels, known as endothelial cells (ECs), attract and direct traveling immune cells to suitable exit sites in the vasculature allowing cells to enter underlying tissue. The "immunomodulatory ECs" (IMECs) (Amersfoort, 2022) therefore fulfill an important supportive role in guidance and directional migration of trafficking immune cells. During inflammation ECs expose a variety of adhesion molecules at their surface that slow down and arrest traveling immune cells in the blood circulation. These adhesive molecules are thought to provide guidance cues to immune cells where to breech the blood vessel wall through a multi-step process known as trans-endothelial migration (TEM) or diapedesis (Schimmel 2017).

During the normal hair growth cycle, only scattered immune cells can be found around and very occasionally within the bulb of an anagen HF (Lintzeri, 2022). But in Alopecia Areata (AA), genetic or exogen factors trigger important unwanted CD8+ T cells trans-endothelial migration (TEM), among others, from the vascular system towards the hair follicle.

Histologically, AA lesions show a characteristic, dense perifollicular and intrafollicular inflammatory cell infiltrate around the bulb area, resembling a swarm of bees, forcing the HF into premature catagen phase, dystrophy and eventually apoptosis. CD8+ T cells are typically the first cells to penetrate into intrafollicular locations, severely disturbing the integrity of the HF (Lintzeri, 2022).

During the flare-ups of AA, the anagen phase of the hair growth cycle is significantly shortened, leading to acute onset of non-scarring hair loss ranging from small circumscribed patchy areas on the scalp, to complete scalp and body hair loss. Although the exact etiology of AA is not yet fully elucidated, it is recognized that the HF bulb IP collapse plays a critical role in the pathophysiology of the disease. What exactly causes this IP collapse is not fully understood yet.

Local inflammation in AA is largely mediated by the JAK-STAT pathway. In AA, there is an overexpression of pro-inflammatory cytokines, which signal through their receptors via the JAK/STAT pathway. This results in JAK-mediated IFN-γ and IL-15 production, which promotes the inflammatory feedback loop that further contributes to local inflammation. Considering the crucial role of JAK-STAT pathway in mediating the CD8+ NKG2D+ T-cell response, a major component of AA pathogenesis, it is no surprise that JAK inhibitor drug class which inhibit the JAK enzymes, interfere with the JAK-STAT signaling pathway, and thereby block the downstream signaling of different cytokines, preserving thereby hair follicle from damage and the onset of new anagen phase, and hair regrowth (Dillon, 2021).

A first JAK inhibitor has been approved for the treatment of AA in 2022, representing the first approved treatment for this debilitating chronic autoimmune disease, and many more are under development (Dillon, 2021). Since the approval of the first JAK inhibitor in 2011 for the treatment of rheumatoid arthritis (Shawky, 2022), real-world evidence of serious health-associated risks has been gathered (Hoisnard, 2022), leading to a JAK inhibitor, class-wide, black-box warning by the US Food and Drug Administration and the European Medicines Agency (Kragstrup, 2022).

Because of the serious risks associated with JAK inhibitors immunosuppression, punctual drug holidays are warranted.

However, since JAK inhibitors "only" block the JAK-STAT signaling pathway, treatment discontinuation systematically leads to a quick and merely total disease relapse of the disease within 3 months (Askin, 2021). Tissue resident memory T cells (TRM) are long-lived lymphocytes that reside in tissues and develop after a T cell-mediated immune response is initiated. In fact, endothelial cells are obligate interaction partners for T cells trafficking into inflamed tissues, consequently may drive TRM development. Wienke et al. have demonstrated, in a co-culture system of human cytokine-activated EC and FACS-sorted T cells, that T cell interaction with activated ECs primes for tissue-residency (Wienke, 2022). The recurrence of AA, the confirmed upregulation of TRM cells, and the reported clinical benefit of JAK inhibitors during administration, support the crucial role of TRM cells in disease pathogenesis (Ryan, 2021).

Before the approval of a first drug for AA, standard of care consisted of the off-label use of corticosteroids mainly, in addition to an older immunosuppressants (Meah, 2020). Unfortunately, corticosteroids, and especially topical corticosteroids (TCS), are documented to induce potential local side effects, including impairment of the epidermal barrier function and skin atrophy (Wollenberg 2018). Additionally, percutaneous absorption of TCS through the disrupted skin may lead to systemic exposure and subsequent growth impairment (Coureau 2008). As a result of both actual and perceived side-effect and potential long-term toxicity, adherence to TCS is often poor due to "corticophobia" (Stalder 2017).

The same way, and because of the serious risks associated with corticosteroids, punctual drug holidays are warranted. However, similarly to JAK inhibitors, disease relapse upon treatment discontinuation is the rule (Lintzeri, 2021).

The systematic disease relapse upon treatment discontinuation transforms AA patients' life in a debilitating "rollercoaster of emotions" (McGettigan, 2013), rhythmed by period of potential hair regrowth upon treatment, followed by period of hair loss after treatment discontinuation.

There is high unmet medical need for a treatment which is both, safe enough not to warrant drug holidays, and which efficacy persists beyond treatment interruption.

SUMMARY

This object has been achieved by providing a method of treatment and/or prevention of hair loss in a subject comprises, administering a composition comprising, as active ingredients, effective amounts of an extract of *Allium* species, an extract of Citrus species, an extract of *Paullinia* species and an extract of *Theobroma* species,
- wherein the composition is administered topically for a period of time necessary to detect one or more therapeutic effects consisting of slowing down the loss of hair, stimulating its growth and/or increasing the density of hair,
- and wherein the one or more therapeutic effects persist for at least 8 weeks, at least 12 weeks, at least 16 weeks, at least 20 weeks, at least 24 weeks or more after the last administration of the composition, as evidenced by measuring the severity of alopecia tool (SALT) score.

A further object of the present invention is to provide the use of a composition of the invention in the manufacture of a medicament for the treatment and/or prevention of hair loss in a subject.

A further object of the present invention is to provide a kit for the treatment and/or prevention of hair loss comprising a composition, or composition for use, of the invention.

DETAILED DESCRIPTION

Figure 1:
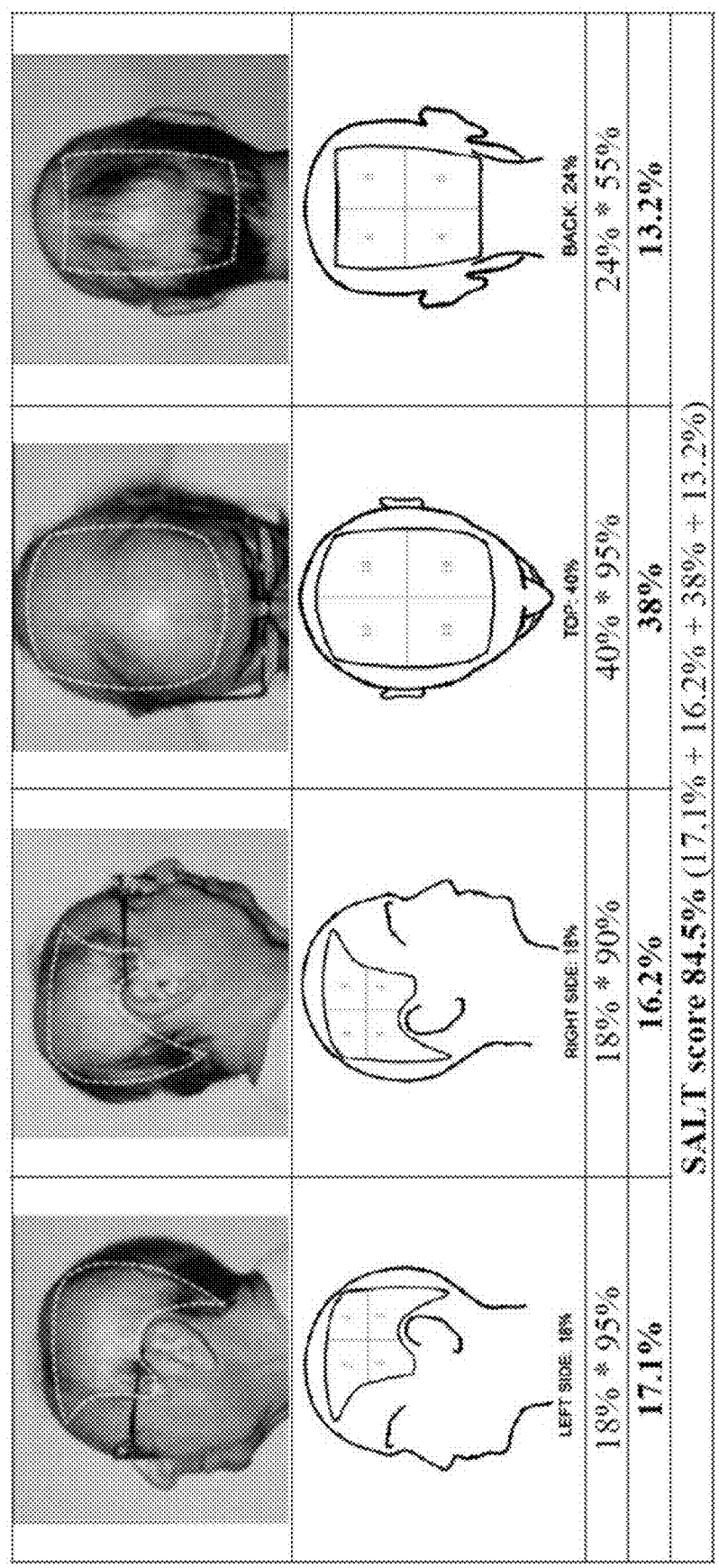
FIG. 1 is a SALT scoring example (adapted from Olsen, 2004).

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise/comprising" is generally used in the sense of include/including, that is to say permitting the presence of one or more features or components. The terms "comprise(s)" and "comprising" also encompass the more restricted ones "consist(s)", "consisting" as well as "consist/consisting essentially of", respectively.

As used in the specification and claims, the singular form "a", "an" and "the" include plural references unless the context clearly dictates otherwise.

As used herein the terms "subject"/"subject in need thereof", or "patient"/"patient in need thereof" are well-recognized in the art, and, are used interchangeably herein to refer to a mammal, including dog, cat, rat, mouse, monkey, cow, horse, goat, sheep, pig, camel, and, most preferably, a human. In some cases, the subject is a subject in need of treatment or a subject with a disease or disorder. However, in other aspects, the subject can be a normal subject. The term does not denote a particular age or sex. Thus, adult and newborn subjects, whether male or female, are intended to be covered. Preferably, the subject is a human, most preferably a human suffering from hair loss or a human that might be at risk of suffering from hair loss.

The term "about," particularly in reference to a given quantity, number or percentage, is meant to encompass deviations of plus or minus ten percent (±10). For example, about 5% encompasses any value between 4.5% to 5.5%, such as 4.5, 4.6, 4.7, 4.8, 4.9, 5, 4.1, 5.2, 5.3, 5.4, or 5.5.

As used herein, "at least one" means "one or more", "two or more", "three or more", etc. For example, at least 8 weeks means 8 weeks or more i.e., 9 weeks, 10 weeks, 11 weeks, etc.

The present invention contemplates methods of treatment and/or prevention of hair loss in a subject.

In one aspect, the method of treatment and/or prevention of hair loss in a subject comprises, administering a composition comprising, as active ingredients, effective amounts of an extract of *Allium* species, an extract of Citrus species, an extract of *Paullinia* species and an extract of *Theobroma* species,
- wherein the composition is administered topically for a period of time necessary to detect one or more therapeutic effects consisting of slowing down the loss of hair, stimulating its growth and/or increasing the density of hair,
- and wherein the one or more therapeutic effects persist after the last administration of the composition, as evidenced by measuring the severity of alopecia tool (SALT) score.

In one aspect, the one or more therapeutic effects persist for at least 8 weeks, at least 12 weeks, at least 16 weeks, at least 20 weeks, at least 24 weeks or more.

The term "treatment" or "treating" means any administration of a composition, pharmaceutical composition, therapeutic agent, active ingredient, compound, etc . . . of the disclosure to a subject for the purpose of:
(i) inhibiting the disease, that is, arresting the development of clinical symptoms;
(ii) reversing the disease, and/or
(iii) relieving the disease, that is, causing the regression of clinical symptoms.

As used herein, the term "prevention" or "preventing" means any administration of a composition, pharmaceutical composition, therapeutic agent, active ingredient, compound, etc . . . of the disclosure to a subject for the purpose of preventing the disease, that is, causing the clinical symptoms and signs of the disease not to develop.

In the context of the present invention, the disease is hair loss. In an aspect, the hair loss is an immune-mediated disease, preferably an autoimmune disease. More preferably, the autoimmune disease is Alopecia Aerata.

Alopecia Areata (AA) is an immune-mediated, autoimmune, inflammatory hair disease affecting both paediatric and adult patients. The immunoinflammatory attack of scalp hair follicles aborts normal hair cycling leading to their early entry in telogen and hair loss. The disease starts with the occurrence of a perifollicular inflammation and invasion of immunoinflammatory cells around the anagen hair bulbs causing HF immune privilege collapse, tissue dystrophy, HF cell death, and hair shaft shedding (Lintzeri-2022). A central role is played by NKG2D+ T cells and natural killer (NK) cells and autoreactive CD8+T-lymphocytes that recognize autoantigens upon exposure of MHC I, II expression on follicular cells. T-cell activation is accompanied by an elevated IFN-γ secretion recruiting or activating more inflammatory cells including macrophages, mast cells, and dendritic cells leading to accelerated cell death and apoptosis of hair follicular cells (Bertolini, M., 2020).

The early clinical manifestations of AA appear as random, patchy hair loss—that may result sometimes in total scalp hair loss (alopecia totalis) or even become generalized to all body parts (alopecia universalis). AA affects patients from all ethnicities, but more women than men, with similar clinical manifestations. Most importantly, when AA starts early in infancy, its prognosis is usually more severe and associated with a higher frequency of unpredictable relapses during adulthood (Villasante Fricke, A. C., 2015).

In one aspect, the subject in need thereof is a subject suffering from mild AA (SALT score<25), moderate AA (SALT core between 25-50), or severe AA (SALT core between 50-95). Preferably, a subject suffering from Alopecia Totalis/Universalis (SALT score>95) is not a subject in need thereof according to the invention and the composition of the invention is not intended to be used to treat such Alopecia Totalis/Universalis.

The term "effective amount" as used herein means a therapeutically effective amount of a composition, pharmaceutical composition, therapeutic agent, active ingredient, compound, etc of the disclosure, high enough to significantly positively modify the symptoms and/or condition to be treated, but low enough to avoid serious side effects (at a reasonable risk/benefit ratio), within the scope of sound medical judgment.

In the context of the present invention, the composition of the invention comprises, as active ingredients, effective amounts of an extract of *Allium* species, an extract of Citrus species, an extract of *Paullinia* species and an extract of *Theobroma* species active *Allium* species, an extract of Citrus species, an extract of *Paullinia* species and an extract of *Theobroma* species.

The term extract, or aqueous-alcoholic extract, of *Allium* species refers particularly to aqueous-alcoholic extracts and native extracts obtained from all species of the genus *Allium* (family Liliaceae) and especially *Allium cepa*.

The term extract, or aqueous-alcoholic extract, of Citrus species refers particularly to aqueous-alcoholic extracts and native extracts obtained from all species of the genus Citrus (family Rutaceae) and especially Citrus lemon.

The term extract (atomised or not), or aqueous-alcoholic extract, of *Paullinia* species refers particularly to aqueous-alcoholic extracts and native extracts obtained from all species of the genus *Paullinia* (family Sapindaceae) and especially *Paullinia cupana*.

The term extract (atomised or not), or aqueous-alcoholic extract, of *Theobroma* species refers particularly to aqueous-alcoholic extracts and native extracts obtained from all species of the genus *Theobroma* (family Malvaceae) and especially *Theobroma cacao*.

In an aspect of the invention, the composition, or composition for use, of the invention is administered topically, usually on external skin surface of the skull, for a period of time necessary to detect one or more therapeutic effects consisting of slowing down the loss of hair, stimulating its growth and/or increasing the density of hair.

The period of time necessary to detect one or more therapeutic effects is usually comprised between about 16 to about 48 weeks, preferably between about 20 to about 40 weeks, more preferably between about 20 and about 32 weeks and even more preferably about 24 weeks.

Any method known in the art may be used to detect, monitor and/or evidence the one or more therapeutic effects consisting of slowing down the loss of hair, stimulating its growth and/or increasing the density of hair.

In one aspect, the one or more therapeutic effects are detected, monitored and/or evidenced by measuring the severity of alopecia tool (SALT) score.

SALT scoring is a calculation based on a scoring system. Scalp is divided into four areas: left side of scalp representing 18% of the scalp surface area, right side of scalp—18% of scalp surface area; top—40% of scalp surface area and back—24% of scalp surface area. The percentage of hair loss in each of the four scalp areas is determined independently, each multiplied by its coefficient (left and right side: 0.18 each; top: 0.40 and back 0.24). The coefficient of each area varies according to the location. Then the resulting hair loss percentages of all four areas are summed up for a final total % hair loss, designated as the SALT score.

Olsen et al. also described a SALT score assessment more suitable for clinical trials. Each area is further subdivided into four quadrants (5%+4%+4%+5%; 10%+10%+10%+10% or 6%+6%+6%+6%) according to the scalp area, see FIG. 1.

The percentage of hair loss in each quadrant is determined independently, each multiplied by its coefficient (0.04, 0.05, 0.06 or 0.1). The coefficient of each quadrant varies according to the location (FIG. 1). Then the resulting hair loss percentages of all four areas (16 quadrants) are summed up for a final total percentage of hair loss, designated as the SALT score.

Due to the numerous calculations to obtain final SALT score and due to the variation of the coefficient depending on the area, manual SALT scoring might be at risk of errors. In one aspect, the SALT scoring is thus computer implemented. In a preferred aspect, the SALT score assessment described by Olsen is used to detect, monitor and/or evidence the one or more therapeutically effects.

Usually, a subject's baseline SALT score is determined before starting the administration of the composition the invention.

In one aspect, a decrease of at least about 2% or more, at least about 5% or more, at least about 10% or more, at least about 15% or more, at least about 20% or more, at least about 30% or more, at least about 40% or more, or at least about 50% or more in SALT score detected when compared to the subject's baseline SALT score indicates that one or more therapeutic effects are detected and that the administration of the composition of the invention is effective.

A decrease of at least about 2% or more, at least about 5% or more, at least about 10% or more, at least about 15% or more, at least about 20% or more, at least about 30% or more, at least about 40% or more, or at least about 50% or more in SALT score detected when compared to the subject's SALT score determined after the last administration of the composition, indicates that one or more therapeutic effects are detected and persist after the stop of said topical administration. In some aspects, the one or more therapeutic effects persist and even improves.

Usually, the composition of the invention is administered topically, preferably on external skin surface of the skull, at least once per day, at least twice per day, or more.

Usually, a volume comprised between about 0.5 ml and 2.5 ml is applied, at least once per day, at least twice per day, or more, in order to cover the whole scalp of the subject.

In one aspect, the composition of the invention comprises from about 65% to about 93% by weight of an aqueous-alcoholic extract of *Allium* species; from about 5% to about 33% by weight of an aqueous-alcoholic extract of Citrus species; from about 0.25% to about 2.5% by weight of an aqueous-alcoholic extract of *Paullinia* species; and from about 0.25% to about 2.5% by weight of an aqueous-alcoholic extract of *Theobroma* species.

In a preferred aspect, the composition of the invention comprises from about 65% to about 93% by weight of an aqueous-alcoholic extract of *Allium cepa*; from about 5% to about 33% by weight of an aqueous-alcoholic extract of Citrus lemon; from about 0.25% to about 2.5% by weight of an aqueous-alcoholic extract of *Paullinia cupana*; and from about 0.25% to about 2.5% by weight of an aqueous-alcoholic extract of *Theobroma cacao*.

In an even more preferred aspect, the composition of the invention comprises about 87% by weight of an aqueous-alcoholic extract of *Allium cepa*; about 12% by weight of an aqueous-alcoholic extract of Citrus lemon; about 0.67% by weight of an aqueous-alcoholic extract of *Paullinia cupana*; and about 0.67% by weight of an aqueous-alcoholic extract of *Theobroma cacao*.

In one aspect, the composition of the invention further contains as excipients from about 0.05% to about 8.0% by weight of sodium chloride and from about 1% to about 40% by weight of glycerine, based on the total weight of the composition.

In one aspect, the composition of the invention comprises from about 0.05% to about 8.0%, preferably from about 0.1% to about 7.0%, more preferably from about 0.4% to about 6.0%, and even more preferably from about 0.9% to about 3% by weight of sodium chloride, based on the total weight of the composition.

In one aspect, the composition of the invention, or composition for use, comprises from about 1% to about 20%, preferably from about 1.2% to about 15%, more preferably from about 1.8% to about 10%, and even more preferably from about 2% to about 5% by weight of glycerine, based on the total weight of the composition.

The compositions of the invention suitable for topical administration include liquid or semi-liquid preparations suitable for penetration through the skin such as solutions, lotions, shake lotions, creams, ointments, gels, foams, transdermal patches, powders, solids, sponges, tapes, vapors, pastes, tinctures, microparticles, microcapsules, nanoparticles, liposomes, or emulsions. Preferably, the compositions of the invention suitable for topical administration are in the form of solutions or lotions.

The present invention further contemplates the use of a composition of the invention in the manufacture of a medicament for the treatment and/or prevention of hair loss in a subject, comprising, administering the medicament comprising, as active ingredients, effective amounts of an extract of *Allium* species, an extract of Citrus species, an extract of *Paullinia* species and an extract of *Theobroma* species, wherein the medicament is administered topically for a period of time necessary to detect one or more therapeutic effects consisting of slowing down the loss of hair, stimulating its growth and/or increasing the density of hair, and wherein the one or more therapeutic effects persist for at least 8 weeks, at least 12 weeks, at least 16 weeks, at least 20 weeks, at least 24 weeks or more after the last administration of the composition, as evidenced by measuring the severity of alopecia tool (SALT) score.

The invention also contemplates kits for the treatment and/or prevention of hair loss as described herein. In one aspect of the invention, the kit comprises a composition of the invention.

The kits of the invention may also comprise a container and a label or package insert on or associated with the container. Suitable containers include, for example, bottles, vials, syringes, dispensers, a spray applicator, etc. The containers may be formed from a variety of materials such as glass or plastic.

The label or package insert may comprise instructions for use thereof. Instructions included may be affixed to packaging material or may be included as a package insert. While the instructions are typically written or printed materials they are not limited to such. Any medium capable of storing such instructions and communicating them to an end user is contemplated by this disclosure.

The present disclosure is to be considered as in all aspects illustrated and not restrictive, the scope of the invention being indicated by the appended Claims, and all changes which come within the meaning and range of equivalency are intended to be embraced therein.

EXAMPLES

Material and Methods

The composition (22.25%) has been evaluated in a clinical trial evaluating the safety and efficacy of the composition in subjects presenting AA (RAAINBOW study, ClinicalTrials.gov identifier NCT03240627). Approximately 1 mL of the composition was applied to whole scalp twice per day, at approximately 12-hour intervals (e.g. in the morning and in the evening)

The RAAINBOW study was a double-blind, randomized, multi-center study versus placebo. 107 subjects (males and females) were enrolled and serve for safety analysis. Among them 62 within inclusion criteria (i.e. moderate to severe AA) representing the Full Analysis Set population (FAS) were analyzed for efficacy.

Results

Below is the summary of the safety analysis.

| Characteristics | Composition (N = 71) | | Placebo (N = 36) | |
|---|---|---|---|---|
| | n % | E | n % | E |
| Any AEs | 28 (39.4%) | 62 | 17 (47.2%) | 42 |
| Any SAEs | 0 | | 1 (2.8%) | 2 |
| Any TEAEs | 28 (39.4%) | 58 | 17 (47.2%) | 38 |
| Drug-related TEAEs | 4 (5.6%) | 5 | 4 (11.1%) | 4 |
| Severe TEAEs | 1 (1.4%) | 1 | 1 (2.8%) | 2 |
| Serious TEAEs | 0 | | 1 (2.8%) | 2 |
| TEAEs Leading to Drug Withdrawn | 1 (1.4%) | 1 | 0 | |
| TEAEs Leading to Drug Interruption | 1 (1.4%) | 1 | 0 | |
| TEAEs Leading to Death | 0 | | 0 | |

[1] Percentages are computed using N provided in the Column header.
[2] AE: Adverse Event, TEAE: Treatment Emergent Adverse Event, n: Number of subjects; E-Number of Events No subjects of the composition group presented a serious adverse event (AE). Only 5.6% of compositing-treated subjects presented an AEs presumably related to the drug (VS 11.1% in the Placebo group). One AE was severe, consisting of severe scalp and face eczema. However, eczema is the most common comorbidity of AA and patients with AA are more likely to have atopic dermatitis, eczema (17.4% vs. 2.2% controls) (Conic, 2020). All other AEs were mild, moderate, local and transient.

None of side-effects observed with JAK inhibitors and corticosteroids have been reported in this study. The composition is extremely safe in the treatment of AA and warrants therefore no treatment discontinuation periods. Therefore, the composition can be used in chronic fashion with no risk to users' health, or risk of disease relapse, in the absence of discontinuation.

Additionally, the RAAINBOW study was designed specifically to evaluate not only the composition efficacy on AA after 6 months of treatment, but also, the potential disease relapse after treatment discontinuation, as measured 6 months after discontinuation.

AA was evaluated through the scalp alopecia areata severity score, known as the SALT (Severity of Alopecia Tool) score, based on global standardized scalp photographs. SALT score was developed in 2004 by Olsen (Olsen, 2004) "to help facilitate well-controlled clinical trials for alopecia areata". It consists of a standardized method to assess the extent of alopecia, a SALT score of 100% consisting of full-baldness. It is based on a 4 pictures-based scoring system, where each side of the head is split into 4 quadrants, and scored by the investigator accordingly (see FIG. 1). The SALT score is the standard measurement endpoint, used by all trials evaluating new treatments efficacy in AA. An example is proposed below.

In the RAAINBOW study, SALT score (FIG. 1) was measured at baseline (V1), after 3 months (V2) and 6 months of treatment (V3). Treatment was then discontinued, and patients' AA was assessed again after 3 months (V4) and 6 months of treatment-free follow-up (V5).

After testing the normality assumption of the data (using both the Q-Q plot and Shapiro-Wilk test), a generalized linear model (GLIMMIX procedure in SAS) was given a preference over the MMRM. The GLIMMIX model had the rank of relative change from baseline in SALT score as the dependent variable and treatment, visit, treatment by visit interaction as fixed effects, and baseline severity based on SALT score as a covariate.

There is a statistically significant difference between the LH-8 and the Placebo arms in terms of relative change, as well as absolute change in SALT score from baseline to Week 24, with the LH-8 arm showing the higher change. Hence, the planned primary endpoint was met (p-value: <0.0001).

Figure 2:
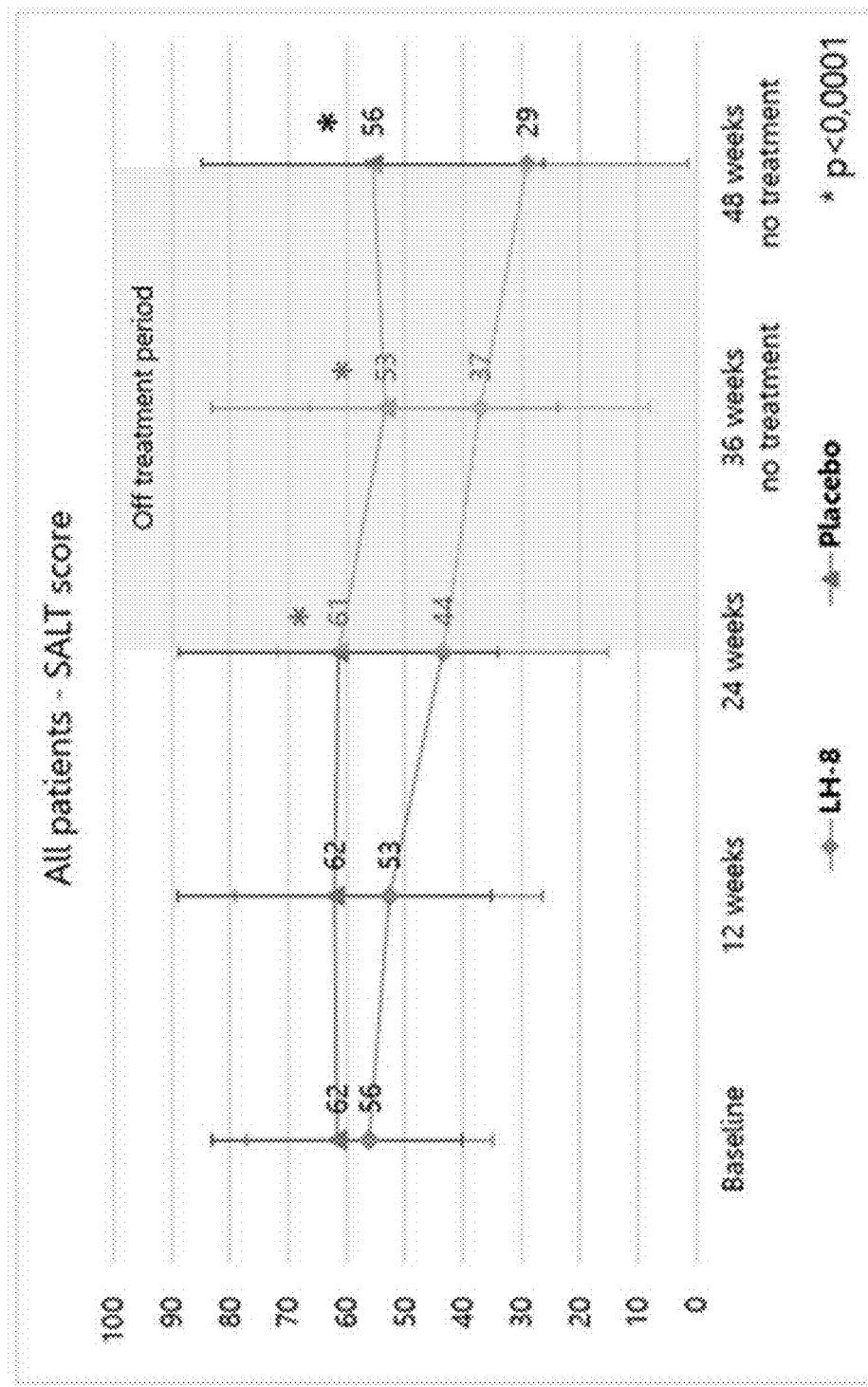
FIG. 2 is a SALT score of the composition-treated patients continued to improve, and the change in SALT score was continuous and statistically significantly superior to placebo throughout the follow-up period.

On the subject treated with the composition who improved during the 6 months treatment period (between V1 and V3), only 4% relapse into the disease after treatment discontinuation, as measured after 6 months of treatment-free period (V5). 96% of the subjects who responded to the treatment did not relapse after treatment discontinuation. Moreover, as illustrated in FIG. 2, the SALT score of the composition-treated patients continued to improve, and the change in SALT score was continuous and statistically significantly superior to placebo throughout the follow-up period.

In chronic conditions, a period of 6 months is considered representative of the disease evolution (Ostbye, 2005). It can be therefore assumed that a treatment-free follow-up period of 6 months is representative of the long-term evolution of the disease (FIG. 2).

In the present case, we can conclude that the discontinuation of treatment with the composition did not lead to disease relapse, except in 4% of the cases. Therefore, unlike with JAK inhibitors, corticosteroids, and although its safety does not warrant discontinuation, the treatment with the composition can be discontinued without risk of disease relapse. While AA is a chronic condition which has so been required chronic treatment, the composition allows not to treat it a chronic manner, but only until the disease is controlled, after which, the treatment can be interrupted safely. This represents a novel way to treat AA.

The invention claimed is:

1. A method of treating alopecia in a human in need thereof, the method consisting essentially of administering therapeutically effective amounts of an extract of *Allium* species, an extract of Citrus species, an extract of *Paullinia* species and an extract of *Theobroma* species to the human in need thereof.

2. The method according to claim 1, wherein the extract of *Allium* species, the extract of Citrus species, the extract of *Paullinia* species and the extract of *Theobroma* species are administered in a composition suitable for topical administration.

3. The method according to claim 1, wherein the alopecia is alopecia aerata.

4. The method according to claim 1, wherein the method consists essentially of administering from about 65% to about 93% by weight of an aqueous-alcoholic extract of *Allium* species; from about 5% to about 33% by weight of an aqueous-alcoholic extract of Citrus species; from about 0.25% to about 2.5% by weight of an aqueous-alcoholic extract of *Paullinia* species; and from about 0.25% to about 2.5% by weight of an aqueous-alcoholic extract of *Theobroma* species.

5. The method according to claim 4, wherein the method consists essentially of administering from about 65% to about 93% by weight of an aqueous-alcoholic extract of *Allium cepa*; from about 5% to about 33% by weight of an aqueous-alcoholic extract of Citrus lemon; from about 0.25% to about 2.5% by weight of an aqueous-alcoholic extract of *Paullinia cupana*; and from about 0.25% to about 2.5% by weight of an aqueous-alcoholic extract of *Theobroma cacao*.

6. The method according to the claim 5, wherein the method consists essentially of administering about 87% by weight of an aqueous-alcoholic extract of *Allium cepa*; about 12% by weight of an aqueous-alcoholic extract of Citrus lemon; about 0.67% by weight of an aqueous-alcoholic extract of *Paullinia cupana*; and about 0.67% by weight of an aqueous-alcoholic extract of *Theobroma cacao*.

7. The method according to claim 2, wherein the composition consists essentially of from about 0.05% to about 8.0% by weight of sodium chloride and from about 1% to about 40% by weight of glycerine, based on the total weight of the composition.

8. The method according to claim 7, wherein the composition consists essentially of from about 0.4% to about 6.0% by weight of sodium chloride and from about 1.2% to about 15% by weight of glycerine, based on the total weight of the composition.

9. The method according to claim 7, wherein the composition consists essentially of from about 0.9% to about 3.0% by weight of sodium chloride and from about 1.8% to about 10% by weight of glycerine, based on the total weight of the composition.

10. The method according to claim 7, wherein the composition consists essentially of from about 0.1% to about 7.0% by weight of sodium chloride, based on the total weight of the composition.

11. The method according to claim 7, wherein the composition consists essentially of from about 1% to about 20% by weight of glycerine, based on the total weight of the composition.

12. The method according to claim 2, wherein the composition is in the form of a solution, lotion, shake lotion, cream, ointment, gel, foam, transdermal patch, powder, solid, sponge, tape, vapor, paste, tincture, microparticles, microcapsules, nanoparticles, liposomes, or emulsion.

13. The method according to claim 2, wherein the composition is administered topically for a period of time necessary to detect one or more therapeutic effects consisting of slowing down loss of hair, stimulating its growth and/or increasing density of hair.

14. The method according to claim 13, wherein the one or more therapeutic effects persist for at least 8 weeks, at least 12 weeks, at least 16 weeks, at least 20 weeks, at least 24 weeks or more after the last administration of the composition, as evidenced by measuring a severity of alopecia tool (SALT) score.

15. The method according to claim 13, wherein the period of time necessary to detect the one or more therapeutic effects is between about 16 to about 48 weeks.

16. The method according to claim 13, wherein the one or more therapeutic effects is detected or evidenced by measuring a severity of alopecia tool (SALT) score.

17. The method according to claim 16, wherein a decrease of at least about 2% or more, at least about 5% or more, at least about 10% or more, at least about 15% or more, at least about 20% or more, at least about 30% or more, at least about 40% or more, or at least about 50% or more in the SALT score is detected when compared to the human's baseline SALT score determined before starting the administration of the composition.

18. The method according to claim 16, wherein a decrease of at least about 2% or more, at least about 5% or more, at least about 10% or more, at least about 15% or more, at least about 20% or more, at least about 30% or more, at least about 40% or more, or at least about 50% or more in the SALT score is detected when compared to the human's SALT score determined after the last administration of the composition.

\* \* \* \* \*